United States Patent [19]

Palmer

[11] Patent Number: 5,439,478
[45] Date of Patent: Aug. 8, 1995

[54] STEERABLE FLEXIBLE MICROSURGICAL INSTRUMENT WITH ROTATABLE CLEVIS

[75] Inventor: Matthew A. Palmer, Miami, Fla.

[73] Assignee: Symbiosis Corporation, Miami, Fla.

[21] Appl. No.: 177,538

[22] Filed: Jan. 5, 1994

Related U.S. Application Data

[63] Continuation-in-part of Ser. No. 42,606, Apr. 2, 1993, abandoned, which is a continuation-in-part of Ser. No. 16,595, Feb. 11, 1993, which is a continuation-in-part of Ser. No. 865,913, Apr. 9, 1992, Pat. No. 5,228,451, which is a continuation-in-part of Ser. No. 521,766, May 10, 1990, Pat. No. 5,133,727, said Ser. No. 42,606, is a continuation-in-part of Ser. No. 16,596, Feb. 11, 1993, which is a continuation-in-part of Ser. No. 680,392, Apr. 4, 1991, Pat. No. 5,192,298, and Ser. No. 989,984, Dec. 4, 1992, Pat. No. 5,293,878, which is a continuation-in-part of Ser. No. 780,014, Oct. 21, 1991, Pat. No. 5,171,258.

[51] Int. Cl.[6] .............................................. A61B 17/28
[52] U.S. Cl. ................................. 606/205; 128/751
[58] Field of Search .......................... 606/205–208, 606/139, 144, 167, 170, 174, 180; 128/749, 751

[56] References Cited

U.S. PATENT DOCUMENTS

| | | | |
|---|---|---|---|
| 1,127,948 | 2/1915 | Wappler | 606/170 |
| 3,895,636 | 7/1975 | Schmidt | 606/205 |
| 4,763,668 | 8/1988 | Macek et al. | 128/751 |
| 4,785,825 | 11/1988 | Romaniuk et al. | 606/174 |
| 4,872,456 | 10/1989 | Hasson | 606/207 |
| 4,945,920 | 8/1990 | Clossick | 606/205 |
| 5,147,373 | 9/1992 | Ferzli | 606/207 |
| 5,176,702 | 1/1993 | Bales et al. | 606/205 |
| 5,201,743 | 4/1993 | Haber et al. | 606/205 |
| 5,254,130 | 10/1993 | Poncet et al. | 606/206 |
| 5,281,230 | 1/1994 | Heidmueller | 606/206 |

FOREIGN PATENT DOCUMENTS

| | | | |
|---|---|---|---|
| 484671 | 5/1992 | European Pat. Off. | 606/170 |
| 3815649 | 11/1989 | Germany | 606/205 |

*Primary Examiner*—Stephen C. Pellegrino
*Assistant Examiner*—Nancy Mulcare
*Attorney, Agent, or Firm*—David P. Gordon

[57] ABSTRACT

A steerable flexible microsurgical instrument is provided with a rotatable clevis. The instrument includes a flexible coil, a flexible pull wire extending through the coil, a clevis which is rotatably coupled to the distal end of the coil, a handle coupled to the proximal end of the coil, and end effectors coupled to the clevis and the pull wire. The clevis is coupled to the distal end of the flexible coil by a bushing which allows axial rotation of the clevis relative to the coil. The pull wire is formed from torsionally obdurate material and is coupled at its distal end to the end effector and at its proximal end to a movable part of the handle. The handle is provided with mechanism for rotating the pull wire relative to the coil and a mechanism for translating the pull wire relative to the coil. Translation of the pull wire relative to the coil moves the end effector relative to the clevis and rotation of the pull wire relative to the coil rotates the clevis and end effector relative to the coil.

22 Claims, 5 Drawing Sheets

STEERABLE FLEXIBLE MICROSURGICAL INSTRUMENT WITH ROTATABLE CLEVIS

This application is a continuation-in-part of Ser. No. 08/042,606, now abandoned, filed Apr. 2, 1993, which in turn is a continuation-in-part of Ser. No. 08/016,595 filed Feb. 11, 1993, which in turn is a continuation-in-part of Ser. No. 07/865,913 filed Apr. 9, 1992, now U.S. Pat. No. 5,228,451, which in turn is a continuation-in-part of Ser. No. 07/521,766 filed May 10, 1990, now U.S. Pat. No. 5,133,727, the complete disclosures of which are hereby incorporated herein by reference. Parent application Ser. No. 08/042,606 is also a continuation-in-part of Ser. No. 08/016,596 filed Feb. 11, 1993, which in turn is a continuation-in-part of Ser. No. 07/680,392 filed Apr. 4, 1991, now U.S. Pat. No. 5,192,298, and Ser. No. 07/989,984 filed Dec. 4, 1992, now U.S. Pat. No. 5,293,878, the complete disclosures of which are hereby incorporated herein by reference.

Application Ser. No. 07/989,984 filed Dec. 4, 1992, now U.S. Pat. No. 5,293,878 is also a continuation-in-part of Ser. No. 07/780,014 filed Oct. 21, 1991, now U.S. Pat. No. 5,171,258, the complete disclosure of which is hereby incorporated herein by reference.

This application is also related to co-owned application Ser. No. 07/680,391 filed Apr. 4, 1991, now U.S. Pat. No. 5,152,778, the complete disclosure of which is hereby incorporated herein by reference.

BACKGROUND OF THE INVENTION

1. Field of the Invention

This invention relates to microsurgical instruments. More particularly, the present invention relates to microsurgical instruments having end effectors mounted on a clevis coupled to an actuation means by a flexible coil where the clevis is rotatable relative to the flexible coil.

2. State of the Art

Most microsurgical instruments used in laparoscopic and endoscopic procedures include a pair of end effectors (cutters, dissectors, extractors, or the like) which are mounted on a clevis, where the clevis is coupled to the distal end of a tube. Proximal ends of the end effectors are often coupled to a push rod which extends through the tube. A handle with an actuation means coupled to the proximal ends of the tube and the push rod is typically used to allow the practitioner to move the push rod relative to the tube, thereby opening and closing the end effectors. In some microsurgical instruments, the tube and push rod are rigid members, such as in parent application Ser. No. 07/989,984. In other instruments, the "tube" is a long flexible coil and the "push rod" is one or more flexible wires such as in parent application Ser. No. 08/042,606.

Instruments utilizing a rigid tube and push rod are typically relatively short and are introduced into the body through a trocar tube. The practitioner views the surgical site through an optical device which is inserted in another trocar tube and "steers" the end effectors to the surgical site by angling the handle of the rigid instrument, and thereby angling the entire instrument. Parent application Ser. No. 07/989,984 discloses means for rotating the end effectors by rotating the rigid tube relative to the handle. This permits the practitioner to adjust the rotational position of the end effectors without changing the rotational position of the handle.

Instruments utilizing a flexible coil and pull wire(s) are typically relatively long and are introduced into the body through the narrow lumen of an endoscope. The practitioner views the surgical site through the endoscope and inserts the long flexible coil of the instrument through the narrow lumen of the endoscope so that the end effectors extend beyond the distal end of the endoscope. Since the flexible coil cannot be steered, the practitioner steers the end effectors to the surgical site by steering the endoscope. The endoscope is typically relatively long and often follows a tortuous path to the surgical site. Although the endoscope can be steered, its tortuous path makes it impossible to rotate. Moreover, because the flexible coil of the surgical instrument is, by nature, torsionally resilient, any attempt to rotate the end effectors by rotating the coil will at best result in a jerking movement of the end effectors. At worst, the coil will deform without effecting any rotation of the end effectors at all.

SUMMARY OF THE INVENTION

It is therefore an object of the invention to provide a microsurgical instrument having a pair of distal end effectors coupled to a proximal handle by a flexible-coil where the end effectors are rotatable.

It is also an object of the invention to provide a microsurgical instrument having a clevis arrangement at the distal end of a flexible coil where the clevis is rotatable relative to the coil.

It is another object of the invention to provide a pull wire for coupling an end effector mounted at the distal end of a flexible coil to a proximal actuation means where the pull wire is torsionally rigid but otherwise flexible.

It is still another object of the invention to provide a handle for a microsurgical instrument having a pair of distal end effectors coupled to the handle by a flexible coil and a pull wire where the handle is provided with manual means for rotating the end effectors.

It is still another object of the invention to provide a handle for a microsurgical instrument having a pair of distal end effectors coupled to the handle by a flexible coil and a pull wire where the handle is provided with means for rotating the pull wire relative to the coil.

In accord with these objects which will be discussed in detail below, the steerable flexible microsurgical instrument of the present invention broadly includes a flexible coil, a handle coupled to the proximal end of the flexible coil, a flexible but torsionally obdurate pull wire extending through the flexible coil, a clevis which is rotatably coupled to the distal end of the coil, and at least one end effector mounted on the clevis. The clevis is coupled to the distal end of the flexible coil by a bushing which allows rotation of the clevis relative to the coil about a longitudinal axis. The pull wire is formed from torsionally obdurate material and is coupled at its distal end to the end effector and at its proximal end to a movable part of the handle. The handle is provided with means for rotating the pull wire relative to the coil and means for translating the pull wire relative to the coil. Translation of the pull wire relative to the coil moves the end effector relative to the clevis and rotation of the pull wire relative to the coil rotates the clevis and end effector relative to the coil.

According to one embodiment of the invention, the handle includes a central shaft with a longitudinal slot about which a displaceable spool with a cross pin is disposed. The central shaft has a thumb ring on its proximal end and longitudinal bore extending from its distal end into the distal end of the slot. The proximal end of the coil extends into the bore on the distal end of the central shaft and is held there by a bushing which allows the central shaft to rotate axially relative to the coil. The pull wire extends through the bore into the slot where it is coupled to the cross pin of the displaceable spool. Longitudinal movement of the spool causes translational movement of the pull wire relative to the coil. Rotational movement of the spool and central shaft causes rotation of the pull wire relative to the coil. A preferred aspect of this embodiment is to provide the thumb ring with a rotational joint so that the central shaft is rotatable relative to the thumb ring.

According to another embodiment of the invention, a lever arm is pivotally engaged to the handle. The proximal end of the flexible coil is fixedly coupled to the handle and the proximal end of the pull wire is coupled to the lever arm by a rotational engagement member. The rotational engagement member is preferably a knurled disk where the pull wire is fixedly coupled to the disk, and the disk is rotationally coupled in a socket of the lever arm. At least a portion of the surface of the disk is exposed by the socket so that the disk may be rotated by the practitioner's finger or thumb.

In either of these two embodiments, a variety of different end effectors may be used including cutters, grippers, forceps and the like. The end effectors may be single acting or double acting and may be coupled to the handle via a single pull wire or multiple pull wires.

Preferred aspects of the rotatable clevis arrangement include providing the clevis bushing with a stepped inner diameter and providing the clevis with a cylindrical stem. The cylindrical stem of the clevis is fitted into the smaller inner diameter portion of the clevis bushing and flared at its proximal end to attach the clevis to the bushing. The larger inner diameter portion of the clevis bushing is fixed to the distal end of the coil by crimping, welding or soldering. The rotational coupling of the clevis and the clevis bushing may be enhanced by the use of friction reducing bearings (e.g. ball bearings or needle bearings) between the clevis stem and the smaller inner diameter portion of the clevis bushing. Alternatively, the clevis stem and/or the smaller inner diameter portion of the clevis bushing may be coated with TEFLON or provided with a TEFLON sleeve.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1A:
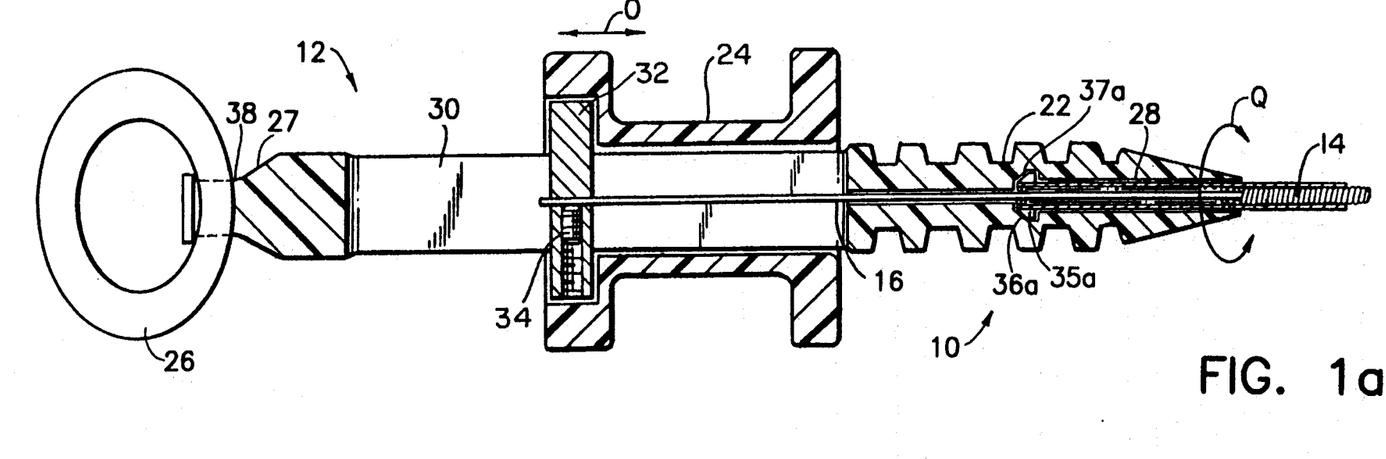
FIG. 1a is a side elevation view in partial longitudinal section of a first embodiment of the proximal end of the microsurgical instrument of the invention.
Figures 2, 3:
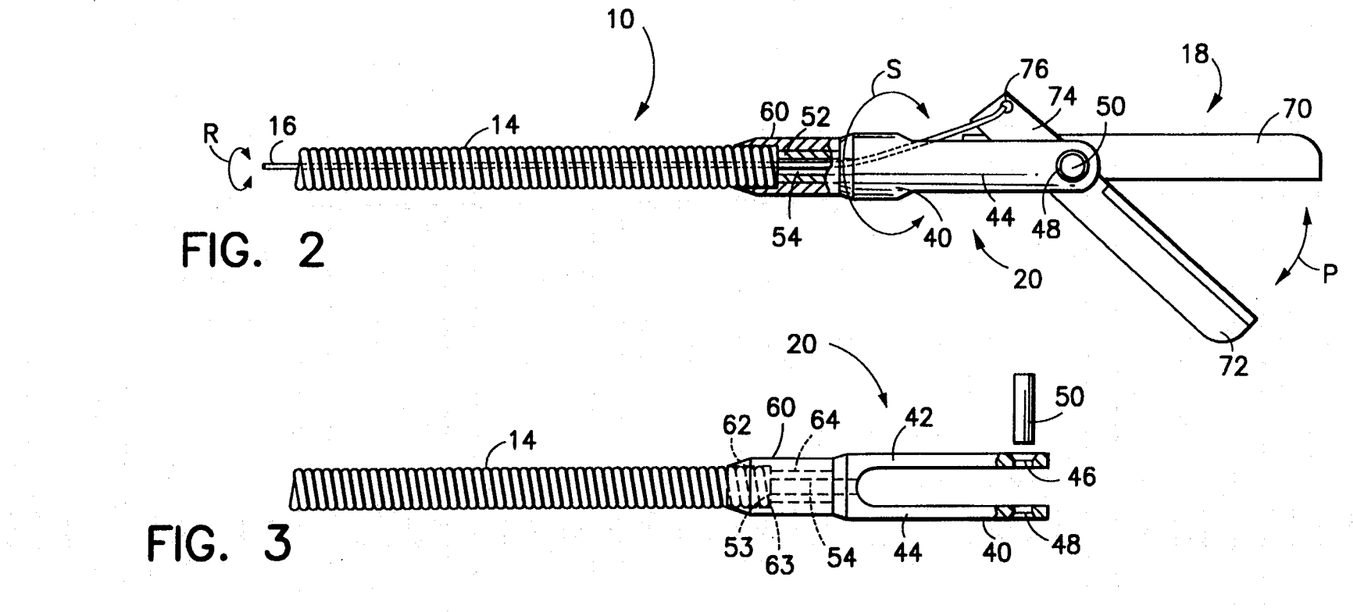
FIG. 2 is a side elevation view in partial longitudinal section of the distal end of a first embodiment of the microsurgical instrument of the invention.
FIG. 3 is a top view of the clevis assembly and coil of FIG. 2.

A first embodiment of the microsurgical instrument 10 of the invention is shown in FIGS. 1a and 2. The instrument 10 includes a proximal handle 12, a flexible member 14 such as a coil which is coupled at its proximal end to the handle 12, a flexible pull wire 16 which extends through the flexible member or coil 14, distal end effectors 18 which are coupled to the distal end of the pull wire 16, and a rotatable clevis assembly 20 which is coupled to the distal end of the coil 14.

The proximal handle 12 of the instrument 10 has a central shaft 22 and a displaceable spool 24. A thumb ring 26 is optionally rotatably coupled to the proximal end 27 of the central shaft 22 and a longitudinal bore 28 is provided at the distal end of the shaft 22. A longitudinal slot 30 extends from the proximal end of bore 28 to a point distal of the thumb ring 26. The displaceable spool 24 is provided with a cross pin 32 which passes through the slot 30 in the central shaft 22. The cross pin 32 is provided with a set screw 34 for engaging the proximal end of the pull wire 16.

Figure 1B:
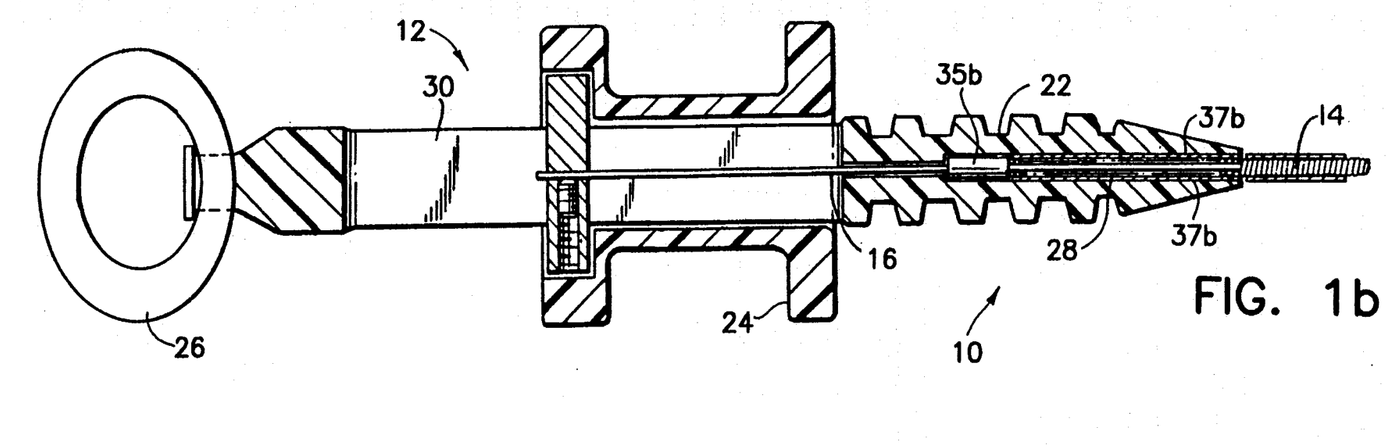
FIG. 1b is a side elevation view in partial longitudinal section of a second embodiment of the proximal end of the microsurgical instrument of the invention.

In accord with a preferred aspect of the invention, the proximal end of the coil 14 is mounted in a stepped longitudinal bore 28 so that the central shaft 22 is axially rotatable relative to the coil 14. According to a first embodiment as seen in FIG. 1a, rotational mounting is preferably obtained by providing a bushing 35a which is mounted in a recess 36a in the bore 28 and which receives the proximal end of the coil 14. The bushing 35a is provided as a frustroconical member 37a which is resiliently deformed as it is pushed into the distal end of the bore 28, and which expands into the recess 36a and is held therein. Of course, if desired, instead of providing a resilient frustroconical member 37a, the central shaft 22 may be formed as a two piece unit, and snapped together, or otherwise joined around the coil 14 and bushing 35a. Alternatively, and as seen in FIG. 1b, a cylindrical body 35b is fixedly mounted at the proximal end of the coil 14 and a sleeve 37b is located distally of the body 35b. The outer diameter of the cylindrical body 35b is larger than the inner diameter of the sleeve 37b. The sleeve 37b is fixedly mounted in the bore 28 by gluing, sonic welding, or the like. The coil 14 is free to rotate within the sleeve 37b and the cylindrical body is free to rotate within the bore 28. The coil 14 is, nevertheless, coupled to the shaft 22 because the cylindrical body 35b prevents the coil 14 from being removed from the sleeve 37b. Regardless, from the foregoing, those skilled in the art will appreciate that rotation of the central shaft 22 relative to the coil 14 results in a corresponding rotation of the displaceable spool 24 and vice versa because of the engagement of the cross pin 32 and the longitudinal slot 30. Moreover, rotation of the central shaft 22 or the displaceable spool 24 relative to the coil 14 results in a rotation of the pull wire 16 relative to the coil 14 because the pull wire 16 is fixed in the spool 24. In accord with the preferred embodiment of the invention, the flexible pull wire 16 is formed as a torsionally rigid member, preferably from drawn, round, straightened 304 V (vacuum melted) stainless steel.

Figure 4:
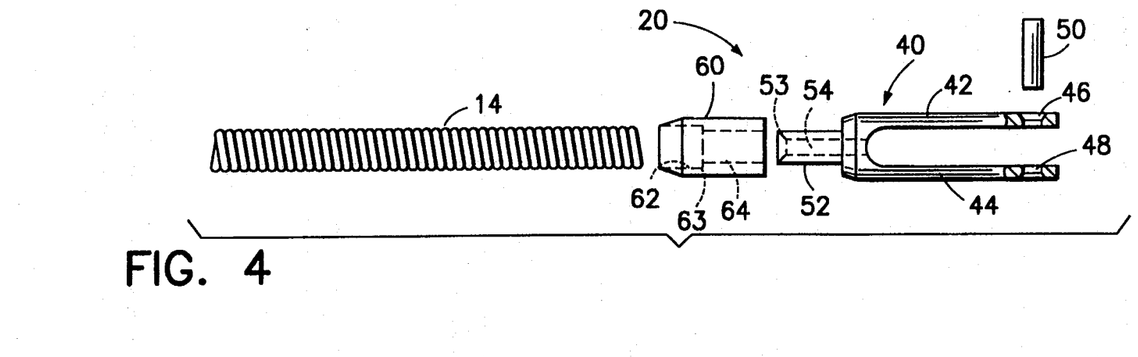
FIG. 4 is an exploded top view of the clevis assembly and coil of FIG. 3.

Turning now to FIGS. 2, 3, and 4, it is seen that the distal end of the coil 14 is coupled to the rotatable clevis assembly 20. The clevis assembly 20 includes a clevis 40 and a clevis bushing 60. Clevis 40 has a pair of clevis arms 42, 44, each of which is provided with an axle hole 46, 48 for receiving a clevis axle 50 upon which the end effectors 18 are mounted in a conventional manner. A cylindrical stem 52 with a throughbore 54 is provided at the proximal end of the clevis 40. The throughbore 54 communicates with the space between the clevis arms 42, 44 and receives the distal end of the pull wire 16 as seen best in FIG. 2. The clevis bushing 60 is provided with a stepped throughbore 62, 64. In particular, the proximal portion 62 of the throughbore has a larger inner diameter than the distal portion 64 of the throughbore, thus creating an annular step 63 in a central part of the bushing 60. The inner diameter of the distal portion 64 of the bushing throughbore is sized to receive the cylindrical stem 52 of the clevis 40. According to a preferred embodiment, the cylindrical stem 52 of the clevis 40 and the distal portion 64 of the bushing throughbore are also sized such that the proximal end 53 of the stem 52 extends beyond the annular step 63 when the clevis and bushing are connected as shown in FIGS. 2 and 3. Further, according to the preferred embodiment, the proximal end 53 of the cylindrical stem 52 is flared after the clevis and bushing are connected so that the clevis stem is held rotatably within the bushing. The flaring may be accomplished by inserting a conical tool into the proximal end 53 of the cylindrical stem 52 or by other techniques. Regardless, after the clevis and clevis bushing are so assembled, the proximal portion 62 of the throughbore of the clevis bushing 60 is attached to the distal end of the coil 14 by crimping, welding or soldering.

Figures 4A, 4B, 4C:
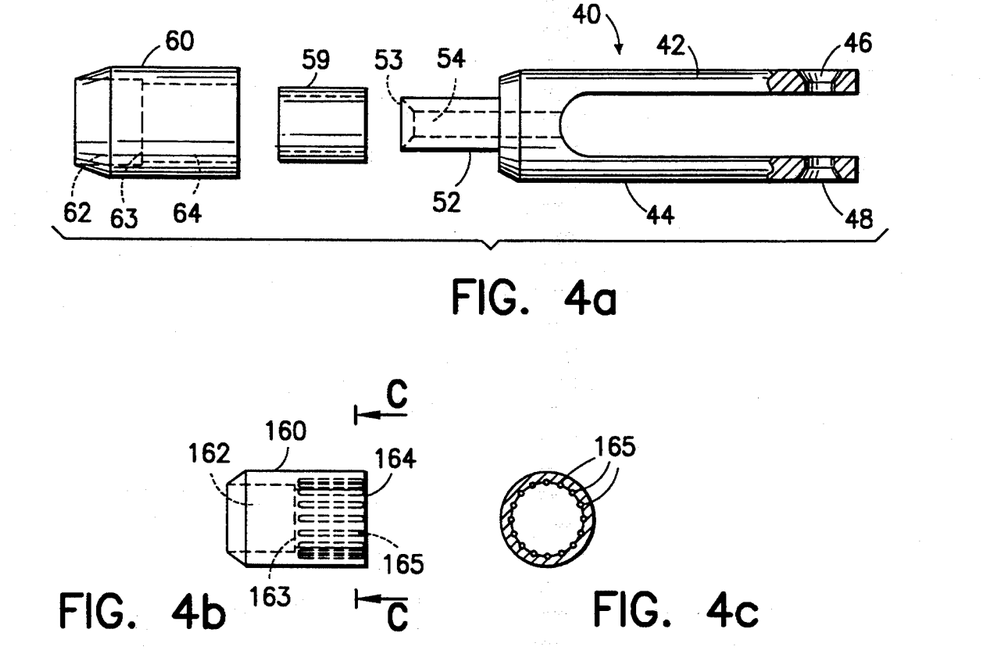
FIG. 4a is an enlarged top view of a second embodiment of the clevis assembly.
FIG. 4b is an enlarged top view of another embodiment of the clevis bushing.
FIG. 4c is a cross sectional view along line C—C of FIG. 4b.

Turning now to FIGS. 4a through 4c, according to the invention, some type of friction reducing means preferably is provided between the clevis 40 and the clevis bushing 60. FIG. 4a shows a TEFLON sleeve 59 which has an inner diameter slightly larger than the outer diameter of the cylindrical stem 52 of the clevis 40 and an outer diameter slightly smaller than the inner diameter of the distal portion 64 of the clevis bushing throughbore. The length of the sleeve 59 is slightly shorter than the length of the distal portion 64 of the clevis bushing throughbore. Those skilled in the art will thus appreciate that the TEFLON sleeve 59 is dimensioned to fit over the cylindrical stem 52 of the clevis 40 before the clevis is attached to the clevis bushing and to thereby provide a lubricious interface between the clevis and the clevis bushing to facilitate their rotational engagement.

FIGS. 4b and 4c show an alternate embodiment of a clevis bushing 160 having a stepped throughbore 162, 164 where the proximal portion 162 of the throughbore has a larger inner diameter than the distal portion 164 of the throughbore, thus creating an annular step 163 in a central part of the bushing 160. According to this embodiment, the distal portion 164 of the clevis bushing throughbore is formed as a race containing a number of radially disposed roller bearings 165. When the clevis 40 is connected to the clevis bushing 160, the cylindrical stem 52 of the clevis is engaged by the roller bearings 165 thereby enhancing the rotational engagement of the clevis and the clevis bushing.

Figure 4D:
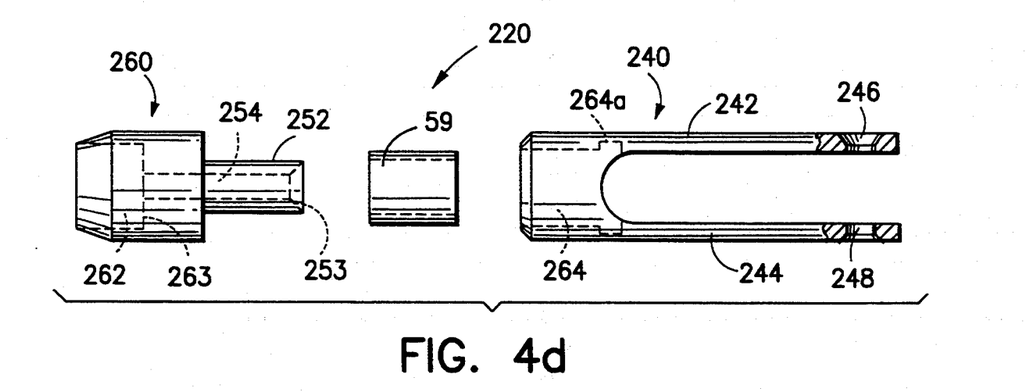
FIG. 4d is an enlarged top view of another embodiment of the clevis assembly.

FIG. 4d shows an alternate embodiment of a rotatable clevis assembly 220. The clevis assembly 220 includes a clevis 240 and a clevis bushing 260. Clevis 240 has a pair of clevis arms 242, 244, each of which is provided with an axle hole 246, 248 for receiving a clevis axle 50 (FIGS. 3 and 4) upon which the end effectors are mounted in a conventional manner. A throughbore 264 having a distal annular step 264a communicates with the space between the clevis arms 242, 244 and provides passage for the pull wire. The clevis bushing 260 is provided with a stepped throughbore 262, 254. In particular, the proximal portion 262 of the throughbore has a larger inner diameter than the distal portion 254 of the throughbore, thus creating an annular step 263 in a central part of the bushing 260. A cylindrical stem 252 is provided at the distal end of the bushing 260. The inner diameter of the clevis throughbore 264 is sized to receive the cylindrical stem 252 of the bushing 260. Preferably, the cylindrical stem 252 of the bushing 260 and the clevis throughbore 264 are also sized such that the distal end 253 of the stem 252 extends beyond the annular step 264a when the clevis and bushing are connected. Further, the distal end 253 of the cylindrical stem 252 is flared after the clevis and bushing are connected so that the bushing stem is held rotatably within the clevis throughbore. The flaring may be accomplished by inserting a conical tool into the space between the clevis arms 242,244 or by other techniques. Regardless, after the clevis and clevis bushing are so assembled, the proximal portion 262 of the throughbore of the clevis bushing 260 is attached to the distal end of the coil or flexible member 14 by crimping, welding or soldering.

As described above with reference to FIGS. 4a–4c, some type of friction reducing means preferably is provided between the clevis 240 and the clevis bushing 260. FIG. 4d shows a TEFLON sleeve 59 which has an inner diameter slightly larger than the outer diameter of the cylindrical stem 252 of the bushing 240 and an outer diameter slightly smaller than the inner diameter of the clevis throughbore 264. The length of the sleeve 59 is slightly shorter than the length of the clevis throughbore. Those skilled in the art will thus appreciate that the TEFLON sleeve 59 is dimensioned to fit over the cylindrical stem 252 of bushing 260 before the clevis is attached to the clevis bushing and to thereby provide a lubricious interface between the clevis and the clevis bushing to facilitate their rotational engagement.

Figure 4E:
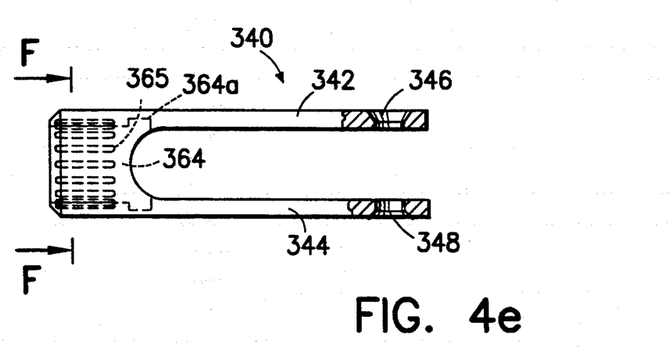
FIG. 4e is an enlarged top view of another embodiment of the clevis.
Figure 4F:
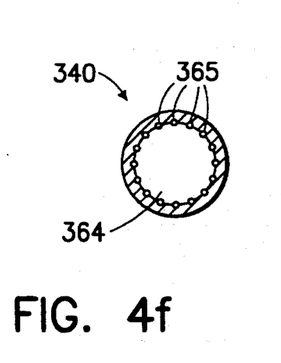
FIG. 4f is a cross sectional view along line F—F of FIG. 4e.

FIGS. 4e and 4f show an alternate embodiment of a clevis 340 having a stepped throughbore 364, 364a. According to this embodiment, the proximal portion of the throughbore 364 is formed as a race containing a number of radially disposed roller bearings 365. When the clevis 340 is connected to the clevis bushing 260, the cylindrical stem 252 of the bushing 260 is engaged by the roller bearings 365 thereby enhancing the rotational engagement of the clevis and the clevis bushing.

Returning to FIG. 2, it is seen that the end effectors 18 in the embodiment of FIG. 2 comprise a single acting scissors having a stationary cutting blade 70 and a movable cutting blade 72. Both of the blades 70 and 72 are mounted between the clevis arms 42, 44 in a conventional manner. The proximal end of the movable cutting blade 72 is provided with a tang 74 having a hole 76 for attachment to the distal end of the pull wire 16. As described more fully in parent application Ser. No. 08/042,606, the pull wire 16 is typically provided with a "jogged" distal end which engages the hole 76 in the tang 74 of the movable cutting blade 72.

Referring now to FIGS. 1a and 2, those skilled in the art will appreciate that translational movement of the spool 24 relative to the central shaft 22 on the handle 12 in the directions indicated by the arrows "O", will result in a translational movement of the pull wire 16 relative to the coil 14. This in turn results in a movement of the movable cutting blade 72 about the clevis axle 50 in the directions indicated by the arrows "P" to thereby effect a cutting action between the blades 70, 72. Moreover, in accord with the invention, it will be appreciated from the foregoing description that rotation of the central shaft 22 and the spool 24 relative to the coil 14 in the directions indicated by the arrows "Q" will result in a rotation of the pull wire 16 relative to the coil 14 as shown by the arrows "R". This results in a rotation of the clevis 40 (240, 340) relative to the clevis bushing 60 (160, 260) in the directions indicated by the arrows "S". It will also be appreciated that such a rotation of the clevis 40 (240, 340) relative to the clevis bushing 60 (160, 260) results in a rotation of the end effectors 18 relative to the coil 14.

In order to operate the instrument of the invention, the practitioner inserts a thumb through the thumb ring 26 of the handle 12 and grasps the spool 24 between the index and middle finger. Translational movement of the pull wire is effected by squeezing the thumb ring and spool like a hypodermic needle. The preferred rotational coupling of the thumb ring 26 with the central shaft 22 allows the practitioner to rotate the spool without removing the thumb from the thumb ring. Alternatively, the practitioner may hold the thumb ring 26 in the palm of the hand with the middle, fourth and fifth fingers, while the thumb and index finger are used to rotate the spool 24.

Figure 5:
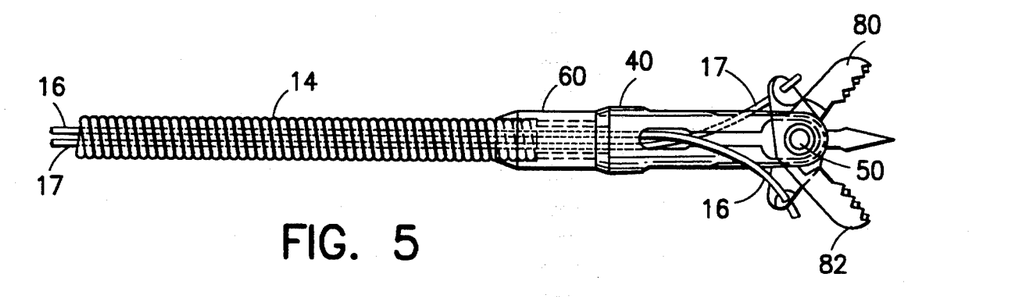
FIG. 5 is a view similar to FIG. 2 showing a double acting biopsy forceps according to a second embodiment of the invention.

As mentioned above, the present invention is not limited to use with any particular type of end effectors. As shown in FIG. 5, for example, a double acting biopsy forceps including a pair of jaws 80, 82 may be provided on the clevis 40. When double acting end effectors are used, an additional pull wire 17, preferably attached to pull wire 16, may be provided within the coil 14. Alternatively, a single pull wire may be used and split into two coupling elements or attached to a Y-adapter which are known in the art.

Figure 5A:
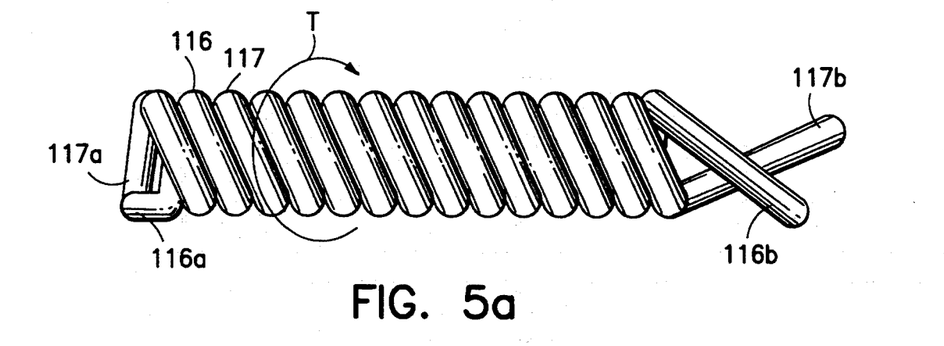
FIG. 5a is an enlarged side elevation view of a first alternate embodiment of pull wires for use with a double acting end effector.

An alternate embodiment of the pull wires 16, 17 is shown in FIG. 5a where a pair of filaments 116 and 117 are soldered or welded together at their proximal ends 116a, 117a and twisted to form a single pull wire having a pair of wound filaments. The separate distal ends 116b, 117b of the filaments are respectively coupled to the tangs of double acting end effectors. Those skilled in the art will appreciate that this embodiment of a pull wire having wound filaments has the characteristic that it is torsionally obdurate in one direction only. For example, as shown in FIG. 5a, the wound filaments 116, 117 are held tightly together when their proximal ends 116a, 117a rotated in the direction "T" and such rotation will result in a corresponding rotation at their distal ends 116b, 117b. Rotation of the proximal ends of the wound filaments in an opposite direction, however, will unwind the filaments prior to effecting any rotation at their distal ends.

Figure 5B:
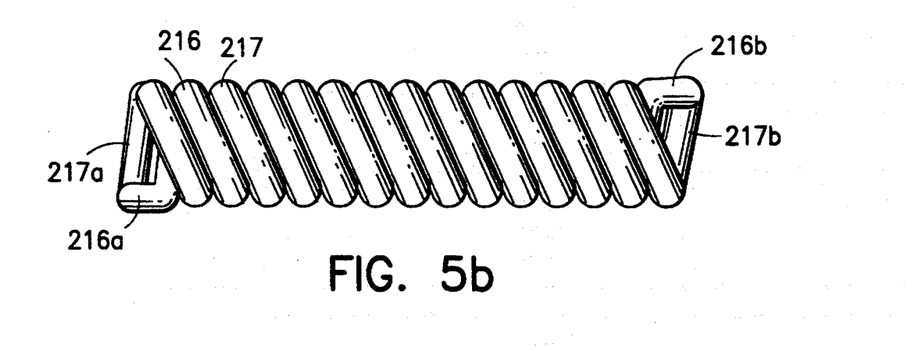
FIG. 5b is an enlarged side elevation view of a second alternate embodiment of pull wires for use with a single acting end effector.

It will be appreciated, that if desired, the "one-way" rotation characteristic obtained by the twisted pull wire embodiment of FIG. 5a can be used in conjunction with a single acting end effector. Alternatively, and as shown in FIG. 5b, a two filament 216, 217 pull wire similar to the pull wire shown in FIG. 5a can be used where the proximal ends 216a, 217a of the filaments are soldered or welded and the distal ends 216b, 217b of the filaments are also soldered or welded. It will be appreciated that with a single acting end effector, the distal ends 216b, 217b are soldered or welded as there is no need to provide two coupling ends of the pull wire.

Figure 6:
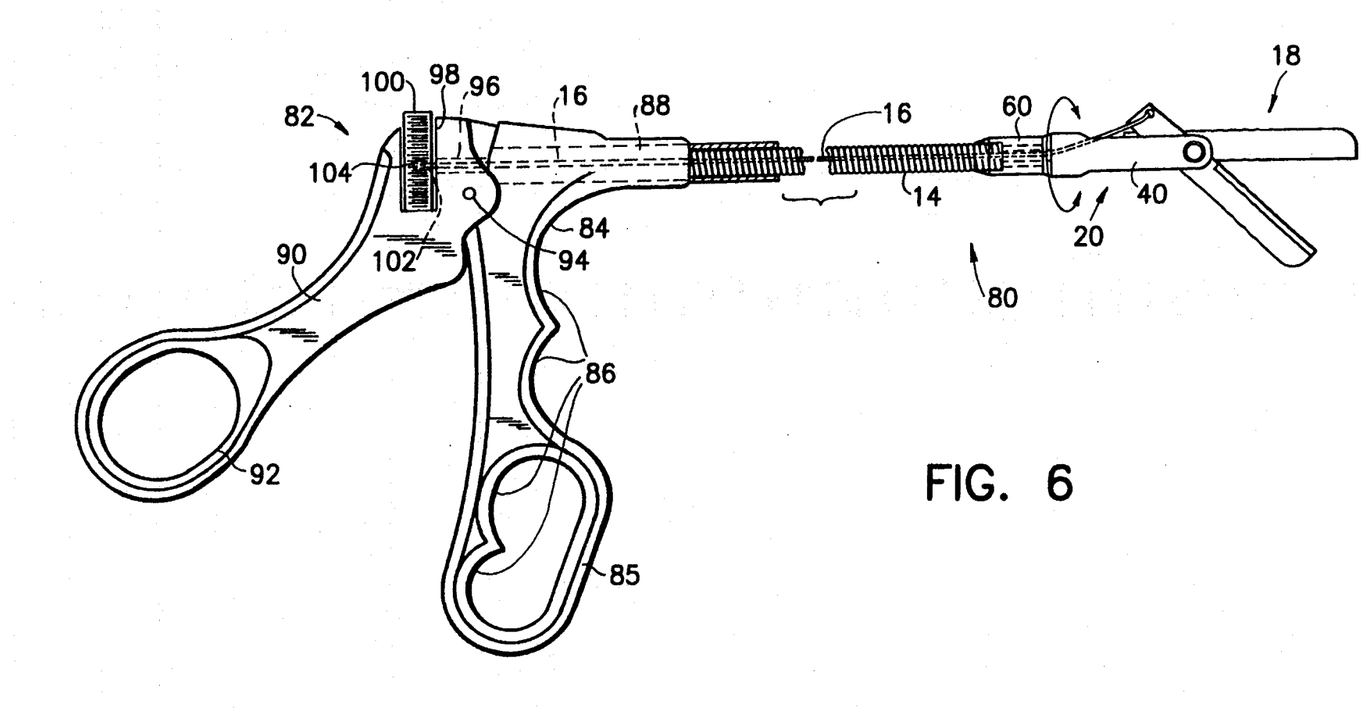
FIG. 6 is a side elevation view in partial longitudinal section of another embodiment of the microsurgical instrument of the invention.
Figure 6A:
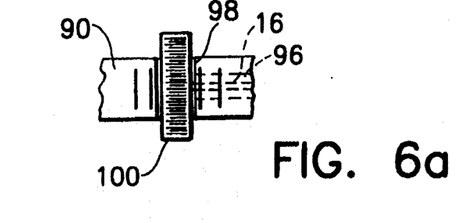
FIG. 6a is a top view of a portion of the lever arm of FIG. 6 showing the rotational engagement of the pull wire with the lever arm.

Another embodiment 80 of the microsurgical instrument is seen in FIGS. 6 and 6a and includes a flexible coil 14, a flexible pull wire 16 extending through the coil 14, distal end effectors 18 coupled to the pull wire 16, a rotatable clevis assembly 20 which is coupled to the distal end of the coil 14, and a proximal actuation assembly 82. In this embodiment, the proximal actuation assembly 82 has a stationary handle portion 84 which is provided with finger recesses 86, two of which are covered by a finger ring 85, and a throughbore 88 for receiving the coil 14 and pull wire 16. A lever arm 90 having a thumb ring 92 is pivotally attached to the stationary handle 84 by a pivot axle 94. The lever arm 90 has a bore 96 which is substantially coaxial with the bore 88 in the stationary handle and a slot 98 which is substantially orthogonal to the bore 96. The slot 98 is fitted with a knurled disk 100 having a pull wire receiving bore 102 and a set screw 104.

The proximal end of the coil 14 is mounted within the throughbore 88 of the stationary handle 84 by crimping, soldering, pressure fit or other suitable method. The proximal end of the pull wire 16 is inserted into the bore 102 of the disk 100 and held in place by the set screw 104. Those skilled in the art will appreciate that the pull wire 16 is therefore rotatable relative to the actuation assembly 82 by rotation of the knurled disk 100 inside the slot 98 in the lever arm 90. It will also be appreciated that movement of the lever arm 90 relative to the stationary handle 84 will cause a translational movement of the pull wire relative to the coil to open and close the end effectors 18. It will further be appreciated that, while the coil 14 and pull wire 16 are preferably flexible, a more rigid tube and rod such as are described in the previously referenced Ser. No. 07/989,984 may be used in lieu thereof. When a more rigid control member is used in place of pull wire 16, the coupling to the knurled disk at the proximal end is preferably accomplished by a ball and socket arrangement.

In operation, the practitioner holds the actuation assembly 82 with fingers wrapped around the recesses 86 and with the thumb inserted in the thumb ring 92. The index finger is free to rotate the disk 100 which effects a rotation of the pull wire 16 and thus a rotation of the clevis 40 and end effectors 18 as described above with reference to the first embodiment of the invention.

There have been described and illustrated herein several embodiments of a steerable flexible microsurgical instrument with a rotatable clevis. While particular embodiments of the invention have been described, it is not intended that the invention be limited thereto, as it is intended that the invention be as broad in scope as the art will allow and that the specification be read likewise. Thus, while particular end effectors have been disclosed, it will be appreciated that other single acting or double acting end effectors could be utilized. Also, while particular handle arrangements have been shown, it will be recognized that other types of handles could be used with similar results obtained. Moreover, while particular configurations have been disclosed in reference to the clevis and the clevis bushing, it will be appreciated that other configurations could be used as well. Further, while the invention was described as having a clevis which is rotatable relative to the coil, it should be appreciated that some rotation of the coil might occur upon rotation of the clevis and the end effectors due to friction. Such rotation of the coil, however, is inconsequential, as it is actually the rotation of the end effectors relative to the endoscope which is desired and which is accomplished by the invention. It will therefore be appreciated by those skilled in the art that yet other modifications could be made to the provided invention without deviating from its spirit and scope as so claimed.

I claim:

1. A surgical instrument, comprising:
   a) a flexible member having a proximal end and a distal end, and a lumen extending therethrough;
   b) a flexible but torsionally unyielding pull wire having a proximal end and a distal end and extending through said lumen of said flexible member;
   c) an actuation means coupled to said proximal ends of said flexible member and pull wire for effecting a translational movement of said pull wire relative to said flexible member, said actuation means including rotation means for effecting a rotation of said pull wire relative to said flexible member;
   d) a bushing having a proximal end and a distal end, said proximal end of said bushing being coupled to said distal end of said flexible member;
   e) a clevis rotatably coupled to said distal end of said bushing; and
   f) at least one end effector coupled to said clevis and coupled to said distal end of said pull wire, said pull wire extending freely through said clevis and said bushing, wherein rotation of said pull wire relative to said flexible member effects a rotation of said at least one end effector and said clevis relative to said bushing and said flexible member.

2. A surgical instrument according to claim 1, wherein:
   said bushing is a cylinder with a stepped inner diameter and said clevis has a cylindrical stem, said bushing embracing said cylindrical stem.

3. A surgical instrument according to claim 2, wherein:
   a larger inner diameter portion of said bushing covers said distal end of said flexible member and said cylindrical stem enters a smaller inner diameter portion of said bushing.

4. A surgical instrument according to claim 3, wherein:
   a proximal end of said cylindrical stem extends proximally of said smaller inner diameter portion and is flared.

5. A surgical instrument according to claim 1, wherein:
   said clevis has a throughbore with a stepped inner diameter and said bushing has a cylindrical stem, said clevis embracing said cylindrical stem.

6. A surgical instrument according to claim 5, wherein:
   said cylindrical stem enters said throughbore of said clevis.

7. A surgical instrument according to claim 6, wherein:
   a distal end of said cylindrical stem extends distally of said throughbore and is flared.

8. A surgical instrument according to claim 1, wherein:
   said actuation means comprises a slotted shaft and a displaceable spool, said proximal end of said flexible member being rotatably coupled to said shaft and said proximal end of said pull wire being coupled to said spool.

9. A microsurgical instrument according to claim 8, wherein:
   said proximal end of said flexible member is coupled to said shaft with a bushing and said shaft is provided with a rotatable proximal thumb ring.

10. A surgical instrument according to claim 1, wherein:
    said actuation means comprises a handle and a lever arm, said proximal end of said flexible member being coupled to said handle and said proximal end of said pull wire being coupled to said lever arm.

11. A surgical instrument according to claim 10, wherein:
    said lever arm is provided with a disk receiving slot, said rotation means comprises a knurled disk and said proximal end of said pull wire is coupled to said knurled disk so that rotation of said knurled disk rotates said proximal end of said pull wire.

12. A surgical instrument according to claim 11, wherein:
    said knurled disk has a first bore for receiving said proximal end of said pull wire, a set screw, and a second bore intersecting said first bore and containing said set screw which secures said proximal end of said pull wire in said first radial bore.

13. A surgical instrument according to claim 1, further comprising:
    g) friction reducing means for reducing friction between said bushing and said clevis.

14. A surgical instrument according to claim 13, wherein:
    said friction reducing means is a polytetrafluoroethlene sleeve located between said bushing and said clevis.

15. A surgical instrument according to claim 13, wherein:
    said friction reducing means comprises a plurality of roller bearings located in one of said bushing and said clevis.

16. A surgical instrument according to claim 1, wherein:
    said pull wire is formed from a pair of wound filaments and is torsionally unyielding in one direction only.

17. A surgical instrument according to claim 1, wherein:
said at least one end effector comprises a pair of biopsy forceps jaws.

18. A clevis assembly for use in a surgical instrument having an end effector, said clevis assembly comprising:
a) a clevis member having a base, a first arm, and a second arm, said first and second arms extending distally from said base and defining an end effector mounting space between said first and second clevis arms said clevis member further having a throughbore in said base communicating with said end effector mounting space; and
b) a clevis bushing having a throughbore with a stepped inner diameter with a distal smaller diameter portion and a proximal larger diameter portion, wherein
one of said clevis member and said clevis bushing has a hollow cylindrical stem extending into the throughbore of the other of said clevis member and said clevis bushing, said hollow cylindrical stem coupling said end effector mounting space with said proximal large diameter portion of said bushing, and connecting means connecting said clevis member to said bushing whereby said clevis member is freely rotatable and non-threaded relative to said clevis bushing.

19. A clevis assembly according to claim 18, wherein:
said cylindrical stem extends through said throughbore and said connection means comprises a flared end on said cylindrical stem resisting removal from said throughbore.

20. A clevis assembly according to claim 18, wherein: said cylindrical stem is covered with a friction reducing material.

21. A clevis assembly according to claim 18, further comprising:
c) bearing means disposed between said cylindrical stem and said other of said clevis member and said clevis bushing for reducing friction between said cylindrical stem and said said other of said clevis member and said clevis bushing as said clevis member rotates relative to said clevis bushing.

22. A surgical instrument, comprising:
a) a tube member having a proximal end and a distal end, and a lumen extending therethrough;
b) a torsionally unyielding control member having a proximal end and a distal end and extending through said lumen of said tube member;
c) an actuation means coupled to said proximal end of said tube member and to said proximal end of said control member for effecting a translational movement of said control member relative to said tube member, said actuation means including rotation means for effecting an axial rotation of said control member relative to said tube member;
d) a clevis;
e) means for rotatably coupling said clevis to the distal end of said tube member; and
f) at least one end effector coupled to said clevis and coupled to said distal end of said control member, said control member passing freely through said clevis,
wherein axial rotation of said control member relative to said tube member effects an axial rotation of said at least one end effector and said clevis relative to said tube member.

* * * * *